(12) United States Patent
Chao et al.

(10) Patent No.: US 7,169,568 B2
(45) Date of Patent: Jan. 30, 2007

(54) METHOD FOR SCREENING MOLECULES THAT EXERT A NEUROTROPHIC EFFECT THROUGH ACTIVATION OF NEUROTROPHIN RECEPTORS

(75) Inventors: Moses V. Chao, New York, NY (US); Francis S. Lee, San Francisco, CA (US)

(73) Assignee: New York University, New York, NY (US)

( * ) Notice: Subject to any disclaimer, the term of this patent is extended or adjusted under 35 U.S.C. 154(b) by 396 days.

(21) Appl. No.: 09/982,095

(22) Filed: Oct. 19, 2001

(65) Prior Publication Data

US 2002/0110837 A1    Aug. 15, 2002

Related U.S. Application Data

(60) Provisional application No. 60/255,887, filed on Dec. 18, 2000.

(51) Int. Cl.
*G01N 33/567* (2006.01)
(52) U.S. Cl. .................................................. 435/7.21
(58) Field of Classification Search ................ 435/7.1, 435/7.21
See application file for complete search history.

(56) References Cited

U.S. PATENT DOCUMENTS 5,753,225 A * 5/1998 Clary et al. .............. 424/130.1

* cited by examiner

*Primary Examiner*—Robert C. Hayes
(74) *Attorney, Agent, or Firm*—Browdy & Neimark, PLLC

(57) ABSTRACT

The present invention is directed to a method for screening and identifying molecules that transactivate a neurotrophin receptor and mediate neuronal cell survival in the absence of neurotrophins which uses one or a combination of three different assays. The assays involve detecting the phosphorylation of a neurotrophin receptor, detecting the phosphorylation of phosphotidylinositol 3'-kinase or Akt enzyme, and assessing neuronal cell survival in the absence of neurotrophins.

11 Claims, 8 Drawing Sheets

METHOD FOR SCREENING MOLECULES THAT EXERT A NEUROTROPHIC EFFECT THROUGH ACTIVATION OF NEUROTROPHIN RECEPTORS

CROSS-REFERENCE TO RELATED APPLICATIONS

The present application claims priority under 35 U.S.C. 119(e) from U.S. provisional application No. 60/255,887, filed Dec. 18, 2000, the entire contents of which are hereby incorporated by reference.

GOVERNMENT LICENSE RIGHTS

The experiments performed in this application were supported in part by the National Institutes of Health, Grant No. Rol NS21072-16. The U.S. Government has a paid up license in this invention and the right in limited circumstances to require the patent owner to license others on reasonable terms as provided for by the terms of Grant No. R01 NS21072-16 awarded by the National Institutes of Health.

BACKGROUND OF THE INVENTION

1. Field of the Invention

The present invention relates to activation of neurotrophin receptors and a screening method for molecules that activate neurotrophin receptors in the absence of neurotrophins.

2. Description of the Related Art

Neurotrophins play a prominent role in the development of the vertebrate nervous system by influencing cell survival, differentiation and cell death events (Levi-Montalcini, 1987; Lewin et al, 1996). Neurotrophins also exhibit acute regulatory effects upon neurotransmitter release, synaptic strength and connectivity (Thoenen, 1996; Bonhoeffer, 1996). In addition to promoting axonal and dendritic branching, neurotrophins serve as chemoattractants for extending growth cones in vitro (Gallo et al, 1997). These actions are mediated by neurotrophin binding to two separate receptor classes, the Trk family of tyrosine kinase receptors and the p75 neurotrophin receptor, a member of the TNF receptor superfamily (Chao and Hempstead, 1995). Binding of neurotrophins to Trk receptors results in receptor autophosphorylation and downstream phosphorylation cascades.

Mutations in Trk neurotrophin receptor function lead to deficits in survival, axonal and dendritic branching, long term potentiation and behavior (McAllister et al, 1999; Minichiello et al, 1999; Lyons et al, 1999). NGF, BDNF, NT-3 and NT-4 also bind to the p75 neurotrophin receptor, a potential cell death receptor whose actions are negated by Trk tyrosine kinase signaling (Dobrowsky et al, 1995; Yoon et al, 1998). Therefore, the ability to regulate Trk tyrosine kinase activity is critical for neuronal survival and differentiation.

Neurotrophic factors exemplified by the neurotrophins (NGF, BDNF, NT-3 and NT-4/5), ciliary neurotrophic factor (CNTF) and glial derived neurotrophic factor (GDNF) all utilize intracellular tyrosine phosphorylation to mediate neuronal cell survival (Segal and Greenberg, 1996; Kaplan and Miller, 2000). CNTF acts through a complex of gp130, CNTF receptor and LIF subunits which are linked to JAK/STAT signaling molecules, whereas the GDNF receptor consists of the c-Ret receptor tyrosine kinase and a separate α-binding protein. Actions of the NGF family of neurotrophins are dictated by the Trk family of receptor tyrosine kinases and the p75 receptor, a member of the TNF receptor superfamily. The neurotrophins have been under investigation for some time as therapeutic agents for the treatment of neurodegenerative diseases and nerve injury, such as Alzheimer's disease, amyotrophic lateral sclerosis (ALS or Lou Gehrig's disease), Parkinson's disease, peripheral neuropathy and spinal cord injury, either individually or in combination with other trophic factors such as CNTF.

The first clinical trials using neurotrophic factors have led to failures (Verrall, 1994; ALS CNTF Treatment Study Group, 1996; Miller et al., 1996; Sendtner, 1997; BDNF Study Group, 1999). Although there is abundant evidence that neurotrophic factors provide neuroprotection in a great variety of experimental systems (Hefti, 1997), the therapeutic procedures for delivering these proteins to patients have not been effective. Subcutaneous administration of CNTF and BDNF in ALS patients was unsuccessful because these proteins did not reach the motor neurons of the spinal cord and brain stem. Systemic treatment of these proteins failed to reach the therapeutic target. Another serious problem was gauging the optimal dosages of neurotrophic factors. Under supramaximal concentrations of BDNF, desensitization or a limitation of the supportive actions of BDNF resulted (Vejsada et al., 1994). This was likely due to downregulation of TrkB receptors. Neurotrophins may also lead to opposite effects on neuronal survival and regrowth of axons over long distances (Thoenen, 2001).

Another approach is to deliver these molecules directly into the brain. This procedure overcomes the problems of systemic administration due to the blood-brain barrier and reaching populations of neurons in the central nervous system that do not project to the periphery. This approach also presents logistic problems. A small number of Alzheimer's patients in Sweden have received intraventricular NGF infusion using pumps, based upon rodent studies in which cognitive deficits in rats could be improved with NGF treatment (Fischer et al., 1987). However, several acute side reactions occurred in these patients from NGF infusion, including pronounced pain, that prevented a meaningful assessment of efficacy (Johagen et al., 1998). Many side effects, including weight loss, diarrhea, hyperplasia, increased epileptic and motor activity, have been documented when high levels of neurotrophins have been administered in animal models or in human trials of ALS (ALS CNTF Treatment Study Group, 1996; Kobayashi et al., 1997; Winkler et al., 1997; BDNF Study Group, 1999; Thoenen, 2001). Besides the problems in managing the dose and pharmacokinetics of these proteins in the nervous system, there is also abundant evidence that neurotrophins can cause apoptosis in the nervous system (Rabizadeh et al., 1993; Casaccia-Bonnefil et al., 1998) These observations demonstrate the limitations of intraventricular and intracerebral infusion of neurotrophic factors as therapeutic intervention for neurodegenerative diseases.

G protein-coupled receptors (GPCR) mediate transmembrane signaling for a large number of ligands, including hormones, neurotransmitters, photons, odorants, pheromones and chemokines. These receptors relay signals to heterotrimeric G proteins which directly modulate the activity of enzymes and ion channels. Every receptor has a similar topology with seven membrane-spanning domains and shares an ability to act through a common signaling mechanism. When activated, a receptor associates with guanine nucleotide regulatory proteins, or G proteins. G proteins are associated with the membrane and consist of three subunits, α, β and γ. The G proteins serve to amplify receptor signaling by exchanging GTP for GDP bound to Gα, followed by the dissociation of Gβ and the Gγ subunits from the receptor. Free Gα couples to effector enzymes, such as adenylate cyclase, guanylate cyclase and phospholipases. A number of second messengers, such as diacylglycerol, IP3, cAMP and cGMP are produced and can influence ion channel activities, such as $Ca^{+2}$ and $K^+$ channels (Gudermann et al., 1997).

Many GPCRs are capable of activating the mitogen-activated protein (MAP) kinase signaling pathway, in addition to downstream effector enzymes such as adenylyl cyclase and phospholipase C (Dhanasekaran et al., 1995; van Biesen et al., 1996; Gudermann, 2001). These events result in increased cell division and growth. GPCR signaling is a complex system that involves regulatory feedback desensitization and protein phosphorylation events. The receptors in this superfamily are diverse at the amino acid sequence level and in their functional responses. The natural ligands of different GPCR members range from non-peptide neurotransmitters to odors and light. Other ligands include lipids such as lysophosphatic acid (LPA); eicosanoids such as prostaglandins; amino acids and ions such as glutamate and calcium; peptides and proteins, such as angiotensin, bradykinin and thrombin; and biogenic amines such as acetylcholine, serotonin and melatonin.

While the signaling cascades initiated by GPCRs cause a large number of metabolic responses and give changes in gene expression leading to cell proliferation and differentiation, little attention has been given to their possible involvement in neuronal survival events. For example, induction of mitogenic events has been observed through signaling from several G protein-coupled receptors that result in an increase in receptor tyrosine kinase phosphorylation (Daub et al., 1996 and Luttrell et al., 1999). Transactivation of EGF and PDGF receptors occurs with LPA, thrombin and carbacol, but the functional consequences of this signaling has not been determined. Whether transactivation of neurotrophic factor receptor tyrosine kinases occurs via G protein-coupled receptors has not been demonstrated to date.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for screening and identifying molecules that transactivate a neurotrophin receptor and mediate neuronal cell survival in the absence of neurotrophins. This is a novel and distinct response from GPCR signaling. The method involves using one of three different assays or any combination of the three to identify a small molecule activator of a neurotrophin receptor. One assay involves detecting whether a neurotrophin receptor is phosphorylated after treatment with a candidate small molecule activator by using an anti-phosphotyrosine antibody that recognizes the phosphorylated form of the receptor. A second assay involves detecting whether phosphotidylinositol 3'-kinase (PI3-K) or Akt, both of which are involved in a major survival signaling pathway, is phosphorylated after treatment with a candidate small molecule activator by using an anti-phospho-Akt antibody that recognizes phosphorylated Akt or an anti-phospho-PI3-K antibody that recognized phosphorylated PI3-K. A third assay involves culturing neuronal cells, treated with a candidate small molecule, in the absence of neurotrophins and assessing neuronal cell survival relative to culturing in the presence of neurotrophins.

BRIEF DESCRIPTION OF THE DRAWINGS

In FIG. 2A, different concentrations of adenosine were administered to PC12615 cells for 2 hours or NGF (1 ng/ml) for 10 min. Cells were also treated with CGS21680 at the indicated dose for 2 hours. In FIG. 2B, PC12 cells (615) were treated with adenosine (10 μM) for various times or with 5 ng/ml NGF for 10 min. Phosphorylated TrkA receptors were detected by immunoblot analysis using PY99 anti-phosphotyrosine antibodies. The amount of Trk receptors in each condition was verified by immunoblotting.

In FIG. 3A, PC12 cells (615) were treated with the $A_{2A}$ agonist CGS 21680 (10 nM) and an $A_1$ agonist CPA (10 nM) for 2 hr. ZM 241385 (10 nM), an $A_{2A}$ antagonist, was incubated with the cells for 15 min prior to treatment with adenosine (10 μM) for 2 hours. In FIG. 3B, PC12 cells (615) were incubated with the indicated concentrations of PP1, a Src family kinase inhibitor (Hanke et al, 1996), for 30 min, and then treated with adenosine (10 μM) for 2 hours. Activation of TrkA was assessed by immunoprecipitation and immunoblot analysis using PY99 anti-phosphotyrosine antibody.

In FIG. 6A, NGF-differentiated PC12 cells were prepared and then NGF and serum were withdrawn for 48 hours as described in the Materials and Methods section of Example 1. Upon NGF withdrawal, various concentrations of CGS 21680 (CGS) were added to the media. CON =No Addition. CGS 21680 (10 nM), NGF (50 ng/ml), and IGF-1 (100 ng/ml) were added together with K252a (100 nM), LY294002 (10 μM), or PD98059 (25 μM) upon NGF withdrawal. In FIG. 6B, hippocampal neurons were prepared and B27 was withdrawn for 48 hrs as described in the Materials and Methods section of Example 1. Upon B27 withdrawal, various concentrations of CGS 21680 (CGS) were added to the media. CGS 21680 (10 nM) and BDNF (100 ng/ml) were added together with K252a (100 nM) upon B27 withdrawal. All LDH levels were quantitated and % cell death calculated as described in the Materials and Methods section of Example 1. All bars depict mean+SEM from three independent experiments.

In FIG. 7A, different concentrations of PACAP27 were administered to PC12 (615) cells for 2 hours or NGF (5 ng/ml) for 10 min. In FIG. 7B, PC12 (615) cells were treated with PACAP27 (1 nM) for various times in the presence or absence of K252a (100 nM) or with 5 ng/ml NGF for 10 min. Phosphorylated TrkA receptors were detected by immunoblot analysis using PY99 anti-phosphotyrosine antibodies. The level of Trk receptors for each condition was verified by immunoblotting with anti-Trk antibodies.

DETAILED DESCRIPTION OF THE INVENTION

Figure 1:
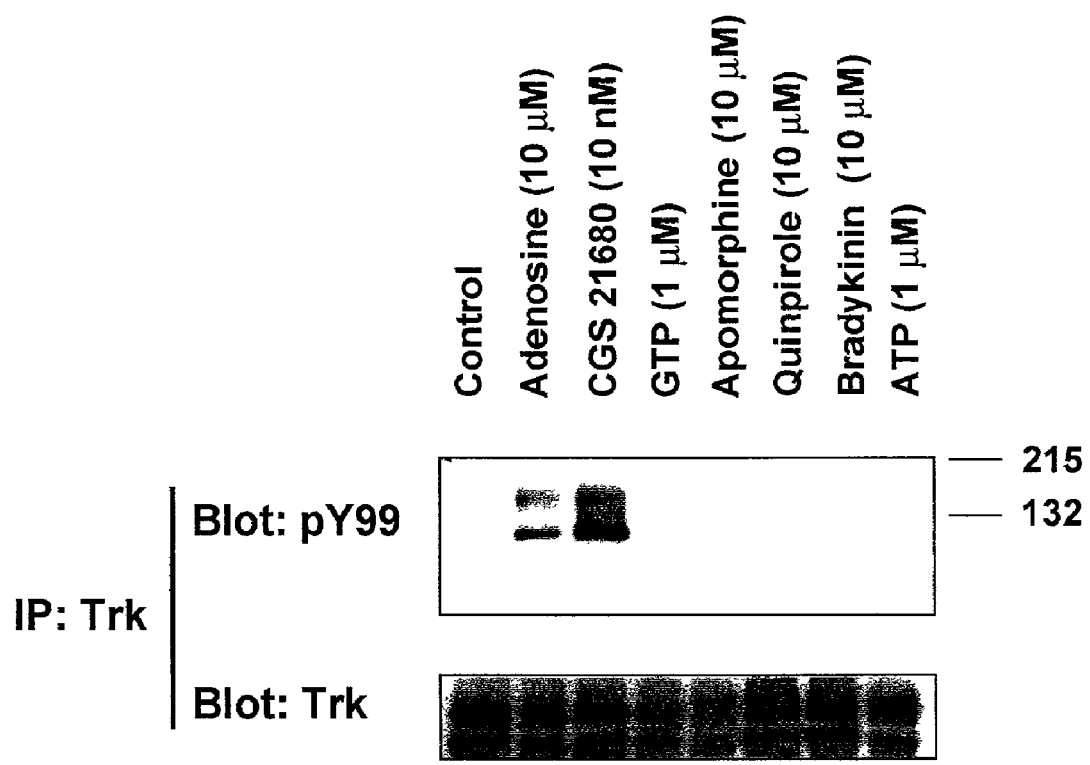
FIG. 1 shows immunoblot analysis on the activation of TrkA receptors with G protein-coupled receptor ligands. Stably transfected PC12 cells expressing high levels of TrkA (615) were treated with the indicated compounds for 2 hours. The cells were subsequently harvested in lysis buffer as described in the Materials and Methods of Example 1. Lysates were immunoprecipitated with anti-pan Trk rabbit antiserum. Immunocomplexes were analyzed by immunoblotting with anti-phosphotyrosine antibody (PY99). Immunoprecipitation of TrkA receptors was then confirmed by immunoblotting of the immunocomplex with anti-pan Trk antiserum.

To explore whether G protein-coupled receptors exert an effect upon neurotrophin receptor signaling, several ligands were tested for their ability to influence TrkA tyrosine kinase activity in PC12 cells in the laboratories of the present inventors as disclosed in Examples 1 and 2. TrkA receptors were immunoprecipitated from PC12 cell lysates and probed with an anti-phosphotyrosine antibody. Activated TrkA NGF receptors were observed with adenosine treatment, but not to nucleotides such as ATP or GTP. Activation of TrkA receptors was also not observed with other G protein-coupled ligands, including bradykinin and dopamine agonists, apomorphine and quinpirole (see Example 1). The specificity of adenosine's effects was also confirmed by the use of CGS 21680, a selective adenosine agonist.

The effect of adenosine upon TrkA receptor activity occurred in a low nanomolar range. A time course of adenosine action showed that the increase in TrkA activation was slow and required at least 90 minutes. This increase was inhibited by K252a, an inhibitor of Trk tyrosine kinases, but was not blocked with anti-NGF antibody pretreatment.

Activation of Trk neurotrophin receptors was also observed in hippocampal neurons after treatment with 10 μM adenosine. Increased Trk tyrosine kinase activity was observed in PC12 cells with the adenosine agonist CGS 21680 and were counteracted by the antagonist ZM 241385, indicating a requirement for adenosine $A_{2A}$ receptors. Survival of PC12 cells and hippocampal neurons after neurotrophin withdrawal was promoted by adenosine, indicating that adenosine can exert a trophic (survival) effect through engagement of TrkA receptors. These results suggest that small molecules may elicit neurotrophic effects for the treatment of neurodegenerative diseases without the use of neurotrophins.

The mechanism by which G protein-coupled receptors are linked to the activation of receptor tyrosine kinases is not understood. Adenosine $A_{2A}$ receptors activate adenylyl cyclase to elevate intracellular cAMP levels via Gαs. Increased cAMP can regulate several pathways, including increasing protein kinase A activity and the MAP kinase pathway. Within 10 minutes of adenosine treatment, a marked increased in phosphorylated MAP kinase was detected in PC12 cells. MAP kinase induction is a rapid response, whereas Trk receptor activation by adenosine followed a slower time course and did not augment MAP kinase activity. This result is in contrast to other examples of G protein-coupled receptor signaling, in which MAP kinase activities are stimulated downstream of the tyrosine kinase receptor.

The effects of adenosine exposure in PC12 cells is mediated through phosphotidylinositol 3'-kinase (PI3-K)/Akt, a major survival signaling pathway. An increase in Akt enzyme activity by adenosine was detected with the same time course as induced Trk autophosphorylation. The activation of Akt activity by adenosine was eliminated by treatment with K252a, an inhibitor of Trk receptors, or LY2494002, a PI3-kinase inhibitor. These results demonstrate that Akt activation by adenosine is Trk- and PI3-kinase-dependent. Adenosine at low concentrations was able to reverse cell death specifically initiated by the withdrawal of trophic support by neurotrophins through the activation of Akt. This establishes a new signaling pathway of ligands for GPCR,

The laboratories of the present inventors have shown that transactivation of Trk tyrosine kinase receptors by adenosine is distinct from other GPCR events. The time course of activation is prolonged and the signaling by adenosine through the Trk receptors gives a survival signal in neurons (as disclosed in Example 1). Transactivation events of this kind have not been demonstrated to date. Furthermore, these findings open up the possibility that adenosine and other related small molecules can be used therapeutically for the treatment of neurodegenerative diseases.

The mechanism by which adenosine transduces trophic effects has not been investigated. Trk receptor signaling mediates a pathway that links adenosine 2A receptors directly to PI-3 kinase/Akt activation (see Example 1). This represents a new mechanism that has not been demonstrated for other GPCR transactivation events. The selective and sustained effects of adenosine on survival suggest that small molecules may be used to target populations of neurons that express both adenosine and Trk receptors. This approach is applicable for a wide number of neurological diseases such as Parkinson's, Alzheimer's diseases, ALS, spinal cord injury and stroke, in which Trk and adenosine receptors are frequently found to be co-expressed in afflicted neuronal populations.

The finding that adenosine can transactivate Trk receptors opens the possibility of identifying or designing new GPCR ligands that can be screened for Trk receptor activation. Described below is a procedure for assessing the activation of Trk and Akt by small molecules which is a preferred embodiment of the invention. In addition to Trk, the glial cell line-derived neurotrophic factor (GDNF) receptor, Ret, is a tyrosine kinase receptor that can also be adapted to this protocol to screen for small molecule activators.

The present inventors have developed a novel screen that uses phosphotyrosine antibodies to detect activated neurotrophic receptors that are activated by GPCR ligands. In the case of Trk receptors, binding to the Trk receptor by anti-phosphotyrosine antibodies that recognize Trk receptor tyrosine residue 684 provides a clear indication that this receptor is activated. This assay is conducted in the absence of neurotrophin ligand and allows for the quick identification of molecules that stimulate trophic receptor signaling. Additionally, another assay as part of the method of the present invention can be used to detect the activation of Akt enzyme activity by the use of phospho-Akt antibodies.

The method of the present invention for screening and identifying molecules that transactivate a neurotrophin receptor and mediate neuronal cell survival in the absence of neurotrophins involves conducting one or a combination of assays A, B or C. Assay A comprises treating neuronal cells with a candidate small molecule activator (transactivator) and then reacting a neurotrophic receptor, such as TrkA and Ret, which is obtained from a cell lysate of the treated neuronal cells, with an anti-phosphotyrosine antibody specific for a phosphorylated form of the neurotrophin receptor. Detection of specific binding of the anti-phosphotyrosine antibody to a phosphorylated form of the neurotrophin receptor identifies a small molecule activator/transactivator of the neurotrophin receptor. In assay B, neuronal cells are also first treated with a candidate small molecule activator/transactivator before reacting either a phosphotidylinositol 3'-kinase, obtained from a cell lysate of the treated neuronal cells, with an anti-phospho-PI3-K antibody specific for the phosphorylated form of PI3-K or an Akt enzyme, obtained from a cell lysate of the treated neuronal cells, with an anti-phospho-Akt antibody specific for the phosphorylated form of Akt. The detection of specific binding of the anti-phospho-PI3-K to. the phosphorylated form of PI3-K or of the anti-phospho-Akt to the phosphorylated form of Akt identifies a small molecule activator/transactivator of a neurotrophin receptor and PI3-K/Akt.

Preferably for assay B, the PI3-K or Akt obtained from a cell lysate of the treated neuronal cells is reacted separately but in parallel to a corresponding anti-PI3-K or anti-Akt antibody. Detecting the specific binding of the anti-PI3-K antibody to PI3-K or of the anti-Akt antibody to Akt provides an assessment of the relative level of phosphorylation of the PI3-K or the Akt enzyme.

Assay C involves culturing neuronal cells in the presence of neurotrophins followed by treating and culturing the neuronal cells with a candidate small molecule activator/transactivator in the absence of neurotrophins. The level of neuronal cell survival in the absence of neurotrophins compared to untreated control neuronal cells (not treated with the candidate small molecule activator/transactivator) in the absence of neurotrophins identifies whether or not the small molecule serves as an activator/transactivator of a neuronal cell survival pathway. A small molecule activator/transactivator will demonstrate an increased level of neuronal cell survival over the untreated control.

While the neuronal cells for use in the method of the present invention is preferably PC12 cells when transactivation of TrkA is assayed, other neuronal cells expressing TrkA can also be suitably used.

A preferred embodiment of the method according to the present invention is as follows:

PC12 cells or cells transfected with Trk receptors (Hempstead et al., 1992) are maintained in Dulbecco's Modified Eagle's Medium containing 10% fetal bovine serum (FBS) supplemented with 100 U/ml penicillin, 100 µg/ml streptomycin, and 2 mM glutamine plus 200 µg/ml G418. Cells are placed in low serum medium (1% FBS, 0.5% horse serum) overnight prior to treatments with candidate small molecules activators. The cells are treated with the candidate small molecule activator for different time periods from 10 minutes to 6 hours. Cell lysates from PC12 are incubated in lysis buffer (1% NP40) for 4 hours to overnight at 4° C. with anti-pan-Trk rabbit polyclonal antibody followed by incubation with protein A-Sepharose beads. Equivalent amounts of protein are analyzed for each condition. The protein A-Sepharose beads are washed five times with lysis buffer and the immune complexes were boiled in SDS-sample buffer and loaded on sodium dodecyl sulfate-polyacrylamide electrophoresis (SDS-PAGE) gels for immunoblot analysis. The immunoreactive Trk receptor are analyzed by immunoblotting with anti-phosphotyrosine antibody (PY99) and detected by ECL reagents (Amersham) based upon enhanced chemiluminescence procedure.

To assess the activity of Akt, endogenous Akt can be immunoprecipitated from lysates with anti-Akt and the proteins assayed in Western blots with anti-phospho-Akt antibodies. Use of the anti-Akt antibody versus the anti-phospho-Akt antibody on lysates can give a comparative assessment of the relative level of the enzyme and extent of activation (Kim et al., 2001).

In a similar manner, dissociated primary cultures of hippocampal neurons from embryonic day 17 (E17) rats can be readily prepared from timed-pregnant Sprague-Dawley rats as described previously (Aibel et al., 1998). Fetuses are removed under sterile conditions and kept in PBS on ice for microscopic dissection of the hippocampus. The meanings are removed and the tissue is placed in Neurobasal media. The tissue is briefly minced with fine forceps and then triturated with a fire polished pasteur pipet. Cells are counted and then plated on culture wells which had been coated with 0.01 mg/ml poly-D-lysine overnight. Hippocampal cells are maintained in Neurobasal media, containing B27 supplement and L-glutamine (0.5 mM) for two weeks. Experiments can be conducted 7 to 10 days after plating.

To assess whether the candidate small molecule activators can keep neurons alive in the absence of neurotrophins, PC12 cells are first differentiated with NGF (50 ng/ml) for 7 days Dulbecco's modified Eagle's medium (DMEM) supplemented with 0.33% fetal bovine serum, 0.67% heat-inactivated horse serum, 2 mM L-glutamine. Serum and NGF are then removed, and candidate molecules are added to the media. After 48 hrs, cell death can be quickly quantified by measuring lactate dehydrogenase (LDH) released from injured cells into the media. LDH values were normalized by subtracting the LDH released by cells maintained in NGF and scaling to full killing induced by 5 min treatment with 1% Triton, an exposure that consistently killed all PC12 cells.

To demonstrate the generality of the method according to the present invention, the laboratories of the present inventors have assessed the ability of ligands from a different class of GPCR from adenosine. Pituitary adenylate cyclase activating polypeptide (PACAP) is a neuropeptide originally isolated from the hypothalamus by its ability to stimulate adenylate cyclase activity of anterior pituitary cells (Miyata et al., 1989). It exists as two forms of 38 and 27 amino acids and is a member of the vasoactive intestinal peptide (VIP)/secretin/glucagon family. The two PACAP peptides interact with GPCR receptors called VPAC1 and PAC1. Recent studies suggested that PACAP has neuroprotective effects in brain and after injury (Takei et al., 2000; Zhou et al., 1999).

To explore whether this GPCR system exerts an effect upon neurotrophin receptor signaling, PACAP was tested for its ability to influence TrkA tyrosine kinase activity in PC12 cells. TrkA receptors were immunoprecipitated from PC12 cell lysates and then probed with an anti-phosphotyrosine antibody, as described above. Activation of TrkA receptors was observed with nanomolar concentrations of PACAP that was inhibited by K252a. In addition, Akt activity was also stimulated by PACAP that depended upon TrkA induction. Similar to the adenosine effects, PACAP's transactivation of Trk receptors required at least two hours of treatment.

Similar effects of PACAP were observed both with the 27 and 38 amino acid peptide forms. Activation of Trk receptors by PACAP was also observed in primary cultures of basal forebrain cholinergic neurons. These results are significant since cholinergic neurons in the basal forebrain degenerate in Alzheimer's disease and these neurons are dependent upon NGF for survival (Hefti, 1986; Williams et al., 1986). PACAP's actions through its GPCR mimics the neurotrophic effects of NGF through transactivation of TrkA receptors.

The identification of small ligands in the G protein-coupled receptor family that regulate tyrosine protein kinase activity in neural cells offers a new strategy for promoting trophic effects during neurodegeneration. An advantage of this approach is the ability to target populations of neurons that express specific GPCR and receptor tyrosine kinases.

Listed below in Table 1 are some non-limiting examples of GPCRs and their corresponding small molecule ligands that may be used in the method of the present invention for screening and identifying molecules that transactivate a neurotrophin receptor and mediate neuronal cell survival in the absence of neurotrophins.

TABLE 1

| Ligand | G Protein-Coupled Receptor |
| --- | --- |
| Adenosine | $A_{2A}R$ |
| Angiotensin II (Iwasaki et al., 1991) | ATR |
| Bradykinin (Yasuyoshi et al., 2000) | BR |
| Chemokines (Aramori et al., 1997) | CXCR, CCR |
| Cholecystokinin (Akaike et al., 1991) | CCKR |
| Dopamine (Le et al., 2001 and Ishige et aL, 2001) | DR |
| Endothelin | ETR |
| Epinephrine/Norepinephrine | β-Adrenergic receptor |
| Gastrin releasing peptide/Bombesin | GRP receptor |
| Shingosine-1-phosphate (Edsall et at., 2001) | EDGR |
| Lysophosphotidic acid | LPA receptor |
| Muscarine (Gurwitz et al., 1995) | mAchR |
| Opioids (Strahs et al., 1997) | μ, δ, κ receptors |
| PACAP | PACR |
| Serotonin (Yan et al., 1997) | 5-HT receptor |
| Somatostatin (Forloni et al., 1997) | SSTR |
| Substance P (Hasenohrl et al., 2000) | NKR |
| Thrombin (Striggow et al., 2001) | PAR |
| Thyrotropin-releasing hormone | TRHR |
| Vasoactive intestinal peptide (Offen et al., 2000) | VPACR |
| Vasopressin (Chen et al., 2000) | VR |
| Melatonin (Reppert et al., 1996) | Mel R |
| Gustatory (Montmayeur et al., 2001) | Taste receptors |
| Odorants (Firestein et al., 2001) | Olfactory receptors |

Another group of neurotrophic factors is the GDNF family, which includes GDNF, neuturin, artemin and persephin. Each protein acts through a single receptor, the Ret receptor tyrosine kinase. The binding of GDNF family members to the receptor complex causes phosphorylation and activation of Ret, which then mediates their physiological effects. GDNF promotes the survival of midbrain dopaminergic neurons and therefore is a promising therapeutic agent in the treatment of Parkinson's disease (Lin et al., 1993; Winkler et al., 1996). GDNF is also a potent survival factor for sensory, sympathetic and ciliary neurons and for axotomized motor neurons.

Mutations in the Ret receptor result in several inherited human diseases, including familial Hirschsprung's disease, which is characterized by the loss of the enteric nervous system and several cancer syndromes such as multiple endocrine neoplasia 2 (MEN2). Interestingly, another set of genes that gives rise to Hirschsprung's disease is endothelin and its receptor, the endothelin receptor B, a member of the GPCR family (Martucciello et al., 2000). Thus, mutations in endothelin and Ret, representing GPCR and tyrosine kinase receptor members, respectively, indicate that these genes lie in a genetic pathway that result in a similar pathogenesis. Furthermore, it suggests there may be transactivation of the Ret receptor by endothelin. Therefore, the prominent role of the Ret receptor tyrosine kinase in neural development and disease suggests that the above approach of identifying small molecules can be applied to the GDNF Ret receptor. A similar assay has been initiated in the laboratories of the present inventors by using the N2a neuroblastoma cell line, which expresses the Ret receptor. Other suitable neuronal cell lines that express the Ret receptor can also be used. Small GPCR ligands that lead to the tyrosine phosphorylation of Ret can therefore be identified by this method.

The activation of GDNF receptors by small molecules overcomes therapeutic problems involved in crossing the blood-brain barrier and other problems associated with the delivery of large proteins to the central nervous system. In the case of GDNF, a small molecule approach would be applicable to not only Parkinson's disease, but also Huntington's disease, in which trophic factor signaling has been shown to be effective in reversing the effects of the huntington protein in neural cells (Saudou et al., 1998). There is also evidence that GDNF and the neurotrophin BDNF are effective at blocking the biochemical effects of drugs of abuse, morphine and cocaine, upon dopaminergic neurons in the ventral tegmental region of the midbrain (Messer et al., 2000). Positive effects of neurotrophic factors in drug-induced changes in neural function suggests that medications that can increase the signaling capacity of neurotrophic receptors may be also useful in addictive disorders.

Having now generally described the invention, the same will be more readily understood through reference to the following examples which are provided by way of illustration and is not intended to be limiting of the present invention.

EXAMPLE 1

This example describes an approach to use small molecule agonists to transactivate Trk neurotrophin receptors. Activation of Trk neurotrophin receptors was observed in PC12 cells and hippocampal neurons after treatment with adenosine, a neuromodulator that acts through G protein-coupled receptors. Theses effects were reproduced by using the adenosine agonist CGS21680 and were counteracted with the antagonist ZM241385, indicating that this transactivation event by adenosine involves adenosine 2A receptors. The increase in Trk activity could be inhibited by the use of the Src family specific inhibitor, PP1, or K252a, an inhibitor of Trk receptors. In contrast to other G protein-coupled receptor transactivation events, adenosine utilized Trk receptor signaling with a longer time course. Moreover, adenosine activated PI3-K/Akt through a Trk-dependent mechanism that functionally resulted in increased cell survival after NGF or BDNF withdrawal. Therefore, adenosine acting through the $A_{2A}$ exerts a receptors trophic effect through the engagement of Trk receptors. This activation with adenosine does not require neurotrophin binding and is observed in PC12 cells, as well as primary cultures of hippocampal neurons. Unlike the results obtained with other tyrosine kinase receptors, increased Trk receptor activity provides increased cell survival over a prolonged time course that requires Akt, and not MAP kinase signaling.

Materials and Methods

CGS 21680, CPA, A23187 and insulin-like growth factor-1 (IGF-1) were purchased from Sigma-RBI. ZM 241385 was from Tocris Neurochemicals, PP1 from Alexis Biochemicals, LY294002 from Biomol, K252a from Calbiochem and PD98059 from New England Biolabs. Nerve growth factor (NGF) was obtained from Harlan Bioproducts and brain derived neurotrophic factor (BDNF) from Peprotech Inc (Rocky Hill, N.J.). All other compounds were from Sigma. Anti-pan-Trk rabbit antiserum raised against the C-terminal region of the Trk receptor was from Barbara Hempstead. Anti-NGF antibody was obtained from Chemicon. Antibodies for immunoblotting included anti-phosphotyrosine and anti-Akt antibodies were from Santa Cruz Biotechnologies, and anti-phospho-Akt, anti-MAP kinase, and anti-phospho-MAP kinase antibodies were from New England Biolabs.

Immunoprotection and Immunoblotting. PC12 cells or PC12-615 cells (Hempstead et al, 1992), were maintained in Dulbecco's Modified Eagle's Medium (DMEM) containing 10% fetal bovine serum (FBS) supplemented with 100 units/ml penicillin, 100 µg/ml streptomycin, and 2 mM glutamine plus 200 µg/ml G418. Cells were placed in low serum medium (1% FBS, 0.5% horse serum) overnight prior to experiments. Cell lysates from PC12, 615 cells, or hippocampal cells were incubated in lysis buffer (1% NP40) for 4 hours to overnight at 4° C. with anti-pan-Trk polyclonal antibody, followed by incubation with protein A-Sepharose beads. Equivalent amounts of protein were analyzed for each condition. The beads' were washed five times with lysis buffer and the immune complexes were boiled in SDS-sample buffer and loaded on sodium dodecyl sulfate-polyacrylamide electrophoresis (SDS-PAGE) gels for immunoblot analysis. The immunoreactive protein bands were detected by ECL reagents based upon enhanced chemiluminescence procedure (Amersham Pharmacia).

$^{125}$I-NGF Binding Analysis. For equilibrium binding studies, $^{125}$I-NGF was prepared as described previously (Hempstead et al, 1989). PC12 cells stably overexpressing TrkA ($2\times10^5$ cells) and HEK 293 cells expressing TrkA ($2\times10^5$) were incubated with $^{125}$I-NGF in the absence and presence of adenosine compounds for 30 minutes at 25° C. The cells were then washed twice with PBS, and $^{125}$I-NGF stripped with an acid solution (0.2 M acetic acid, 0.5 M NaCl). Nonspecific binding was assessed by adding unlabeled NGF at a final concentration of 1000 ng/ml and represented less than 20% of total binding. Specific binding was defined as total binding minus nonspecific binding. All conditions were carried out in triplicate and SEM calculated.

Hippocampal Cell Cultures. Dissociated primary cultures of hippocampal neurons from embryonic day 17 (E17) rats were prepared from timed-pregnant Sprague-Dawley rats as described previously (Aibel et al, 1998). Fetuses were removed under sterile conditions and kept in PBS on ice for microscopic dissection of the hippocampus. The meninges were removed and the tissue was placed in Neurobasal media (Gibco BRL). The tissue was briefly minced with fine forceps and then triturated with a fire polished pasteur pipet. Cells were counted and then plated on culture wells coated with 0.01 mg/ml poly-D-lysine overnight. Hippocampal cells were maintained in Neurobasal media, containing B27 supplement and L-glutamine (0.5 mM). Experiments were conducted 7–10 days after plating.

Cell Death Assay. PC12 cells were differentiated in Dulbecco's modified Eagle's medium (DMEM), supplemented with 0.33% fetal bovine serum, 0.67% heat-inactivated horse serum, 2 mM L-glutamine and NGF (50 ng/ml) for 7 days. Serum and NGF were then removed, and adenosine agonists or growth factors added to the media. After 48 hrs, cell death was quantified by measuring lactate dehydrogenase (LDH) released from injured cells into the media using the Cytox 96 Cytotoxicity Assay Kit (Promega, Madison, Wis.). LDH values were normalized by subtracting the LDH released by cells maintained in NGF (50 ng/ml) and scaling to a full kill (=100%) reference induced by 5 min treatment with 1% Triton, an exposure that consistently killed all PC12 cells.

Hippocampal neurons were maintained in Neurobasal media containing B27 supplement and 0.5 mM L-glutamine for 10 days. B27 was then removed, and adenosine agonists or BDNF (100 ng/ml) was added to the media. MK-801 (1 µM) was added to all conditions, to decrease the contribution of NMDA-mediated cell death. After 48 hrs, cell death was assessed by measurement of LDH released into media. LDH values were normalized by subtracting the LDH released by cells maintained in BDNF (100 ng/ml) and scaling to full kill (=100%) reference induced by 24 hr of treatment with A23187 (30 µM), a condition that resulted in complete cell death of all neurons (Kim et al, 2000).

Results

Transactivation of mitogenic tyrosine kinase receptors through G protein-coupled receptors has been previously described (Daubet et al., 1996; Linseman et al., 1995; Rau et al., 1995). To explore whether any G protein-coupled receptors exert an effect upon neurotrophin receptor signaling, several ligands were tested for their ability to influence TrkA tyrosine kinase activity in PC12 cells. Receptors for each ligand are found on PC12 cells (Etschied et al., 1991; Inoue et al., 1992; Williams et al., 1987; Kim et al., 1994). TrkA receptors were immunoprecipitated from PC12 cell lysates and then probed with an anti-phosphotyrosine antibody. Activated TrkA receptors were observed with adenosine treatment (10 µM), but not with nucleotides such as ATP or GTP (FIG. 1). The TrkA doublet represents an unglycosylated form of 110 kDa and the fully glycosylated form of 140 kDa (Hempstead et al., 1992). Activation of TrkA receptors was not observed with other G protein-coupled ligands, including bradykinin and dopamine agonists, apomorphine and quinpirole (FIG. 1). The specificity of adenosine's effects was also confirmed by the use of CGS 21680, 2-[(4-(2-carboxyethyl)phenylethyl)]aminoadenosine-5'-N-ethylcarboxamide, a selective adenosine $A_{2A}$ agonist (Jarvis et al, 1989).

Figure 2A:
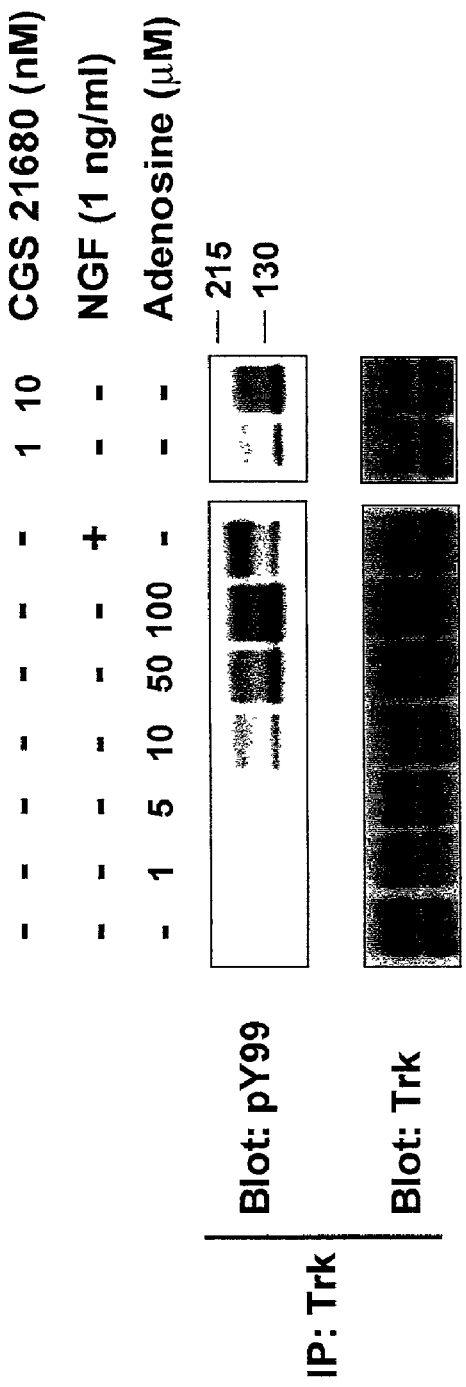
FIGS. 2A and 2B show immunoblot analysis on the time course and close of adenosine activation of TrkA receptors.
Figure 2B:
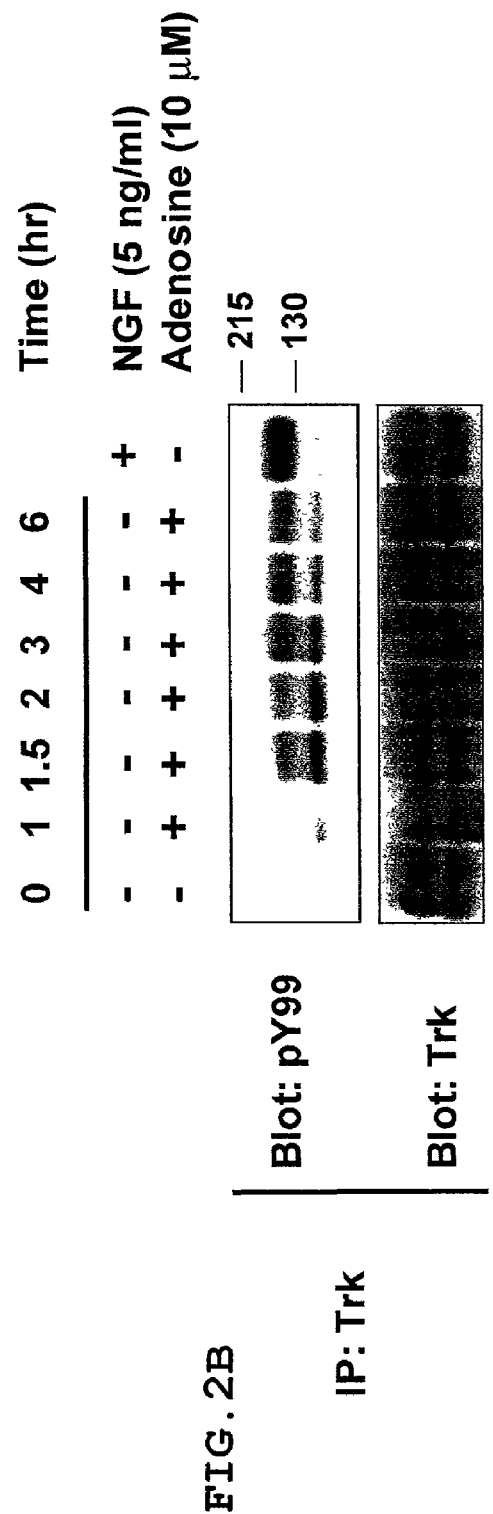

The effect of adenosine upon TrkA receptor activity occurred in a low concentration range (FIG. 2A). This response was verified by the use of 1 nM CSG 21680. A time course of adenosine action showed that the increase in TrkA activation was slow and required at least 90 minutes (FIG.

2B), which is delayed compared to NGF treatment. This increase was inhibited by K252a, a known inhibitor of Trk tyrosine kinases (see below), but was not blocked with anti-NGF antibody pretreatment (data not shown). It is formally possible that adenosine treatment leads to the production of NGF by PC12 cells that could act in an autocrine fashion to stimulate TrkA receptors. This possibility was discounted by the absence of neurite outgrowth activity of supernatants taken from PC12 cells treated with adenosine and by a lack of effect of anti-NGF antibody on adenosine's action (data not shown).

Adenosine interacts with four different G protein-coupled receptors, designated $A_1$, $A_{2A}$, $A_{2B}$, and $A_3$ receptors (Neary et al, 1996). The $A_2$ class of adenosine receptors are expressed in PC12 cells and have been detected by radioligand binding (Williams et al, 1987). Adenosine does not bind to the TrkA receptor. There was no displacement of $^{125}$I-NGF binding with an excess of adenosine (1 mM) or CGS 21680 (1 µM) in PC12 cells overexpressing TrkA (Table 1). As PC12 cells express the p75 neurotrophin receptor which also binds $^{125}$I-NGF, similar experiments were carried out in 293 cells after transfection with TrkA. Again, excess concentrations of adenosine or CGS 21680 did not displace $^{125}$I-NGF binding to 293 cells that expressed TrkA (Table 2). The concentrations of adenosine and CGS 21680 were approximately 100-fold greater than those normally used in $A_{2A}$ receptor binding and signaling studies (Ralevic et al, 1998).

TABLE 2

No Effect of Adenosine on $^{125}$I NGF Binding

|  | Condition | Specific Binding |
|---|---|---|
| Pc12 | Control | 14316 +/− 350 |
|  | Adenosine (1 mM) | 14403 +/− 888 |
|  | CGS 21680 (1 µM) | 14237 +/− 1055 |
| 293/TrkA | Control | 39076 +/− 2885 |
|  | Adenosine (1 µM) | 36618 +/− 4185 |
|  | CGS 21680 (1 µM) | 39568 +/− 2032 |

Figure 3A:
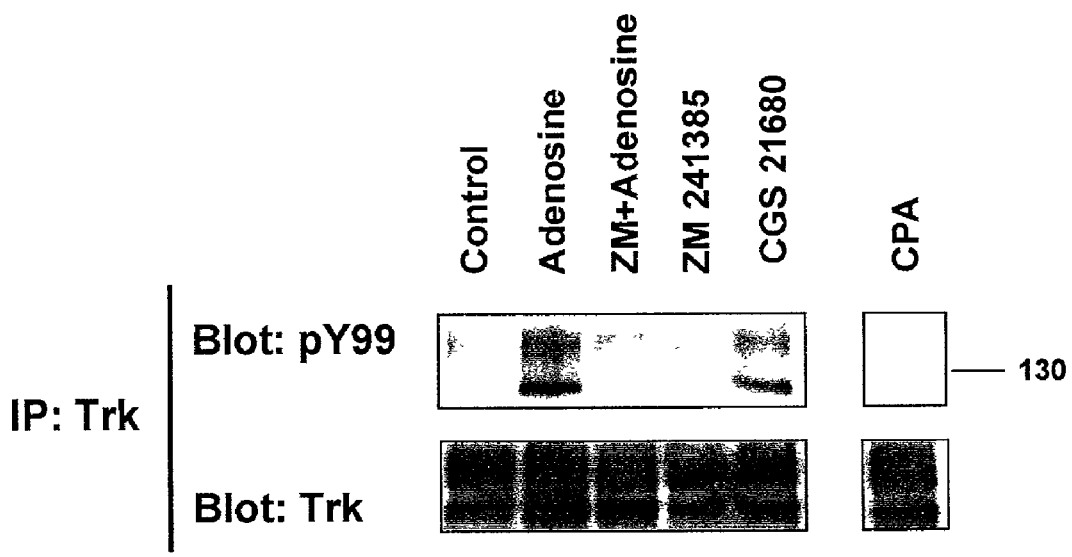
FIGS. 3A and 3B show immunoblot analysis on adenosine activation of TrkA by adenosine $A_{2A}$ receptors.

To verify that adenosine interacted specifically with the $A_{2A}$ receptor, several adenosine analogs were utilized. A low concentration (10 nM) of CGS 21680 gave a similar increase in phosphorylated TrkA receptors with the same time course as adenosine (FIGS. 2A and 3A). In contrast, a selective $A_1$ agonist, CPA, N(6)-cyclopentyladenosine, had no effect (FIG. 3A). Incubation of PC12 cells with the $A_{2A}$ antagonist, ZM 241385, 4-[2-[7-amino-2-(2-furyl)-1,2,4-triazolo[1,5-a](1,3,5)triazin-5-ylamino]ethyl]phenol, that binds the $A_{2A}$ receptor with high affinity (Poucher et al, 1995) antagonized the effects of adenosine on the phosphorylation of TrkA receptors (FIG. 3A). These results are consistent with the involvement of adenosine $A_{2A}$ receptors in mediating the increase in Trk receptor activity.

Figure 3B:
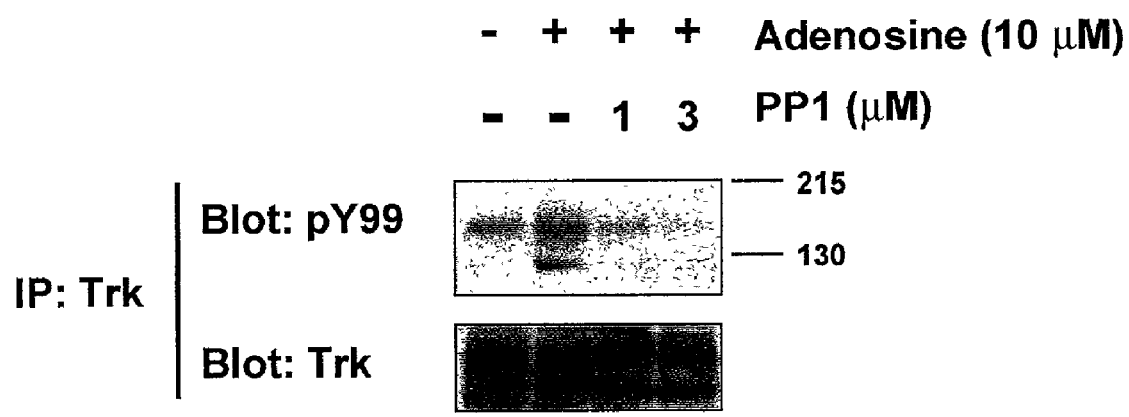

The mechanism by which G protein-coupled receptors are linked to the activation of receptor tyrosine kinases is not well understood. $A_{2A}$ receptors activate adenylyl cyclase to elevate intracellular cAMP levels via Gs. Increased cAMP can regulate several pathways, including increasing protein kinase A activity and the MAP kinase pathway (Seidel et al, 1999). Src family kinases have been implicated as mediators of mitogenic receptor tyrosine kinase transactivation, such as several G protein-coupled receptor agonists, such as lysophosphatidic acid, angiotensin II, thrombin and bradykinin (Luttrell et al, 1999). To test whether a Src family member is involved in the activation of Trk receptors by adenosine, the PP1 inhibitor (Hanke et al, 1996) was used. Treatment of PC12 cells with 1 µM PP1 resulted in a marked decrease in the level of tyrosine phosphorylated TrkA receptors elicited by adenosine (FIG. 3B). Increasing concentrations of PP1 produced a progressively stronger inhibition. These results suggest that the regulation of TrkA activity by adenosine may be mediated by a Src family member. An involvement of Src was previously implicated in NGF signaling downstream of its receptor (D'Arcangelo et al, 1993). However, it is conceivable that members of the Src tyrosine kinase activity may be activated by G proteins. This has been demonstrated for Lck, which acts in thymocytes downstream of the β-adrenergic receptor and whose activity can be increased in vitro by Gs (Gu et al, 2000).

Hippocampal Neurons

Figure 4A:
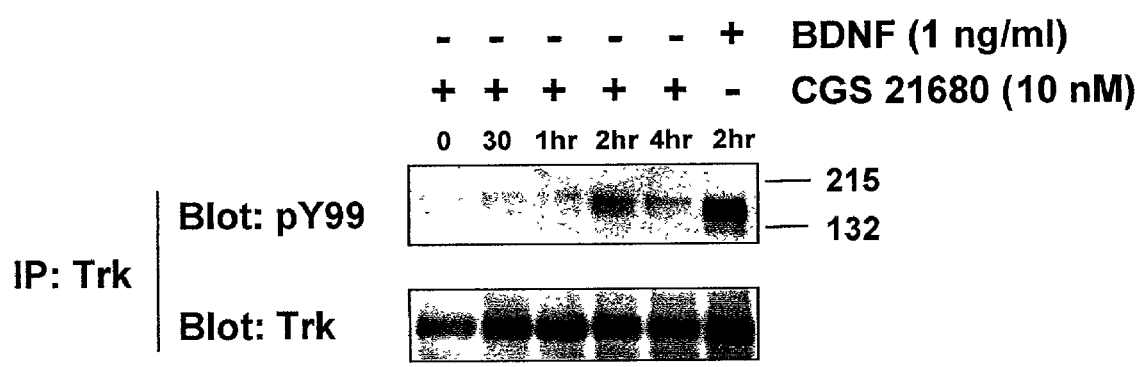
FIGS. 4A and 4B show Western blots on adenosine activation of Trk receptors in hippocampal neurons. Primary cultures of E17 hippocampal neurons were prepared as described in the Materials and Methods of Example 1 and treated with (FIG. 4A) CGS 21680 (10 nM) or BDNF (1 ng/ml) for various times and (FIG. 4B) either adenosine (10 μM), CGS 21680 (10 nM), CPA (10 nM) or BDNF (10 ng/ml) for 2 hr. Activation of TrkA receptors was assessed by immunoprecipitation and Western blotting with anti-phosphotyrosine antibody.
Figure 4B:
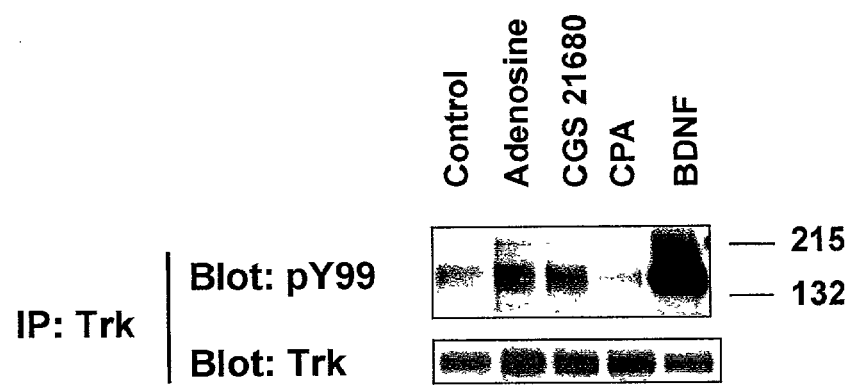

To extend the generality of adenosine effects on Trk receptors, we established primary hippocampal neuronal cultures from rat embryos at E17. Hippocampal neurons predominantly express the TrkB receptor, but not TrkA receptors, and also express and $A_1$ and $A_{2A}$ receptors (Dixon et al, 1996). Treatment with 10 µM adenosine or 10 nM CGS 21680 for two hours gave rise to phosphorylated TrkB receptors in hippocampal neurons (FIGS. 4A and 4B), similar to the activation of TrkA receptors by adenosine. An $A_1$ specific agonist, CPA, however, did not activate TrkB receptors (FIG. 4B), confirming the specificity of this effect to the $A_{2A}$ receptor. These results not only extend the effects of adenosine to hippocampal neurons, but also demonstrate that TrkB can also be activated by signaling through the $A_{2A}$ receptors.

Downstream Signal Transduction

Figure 5:
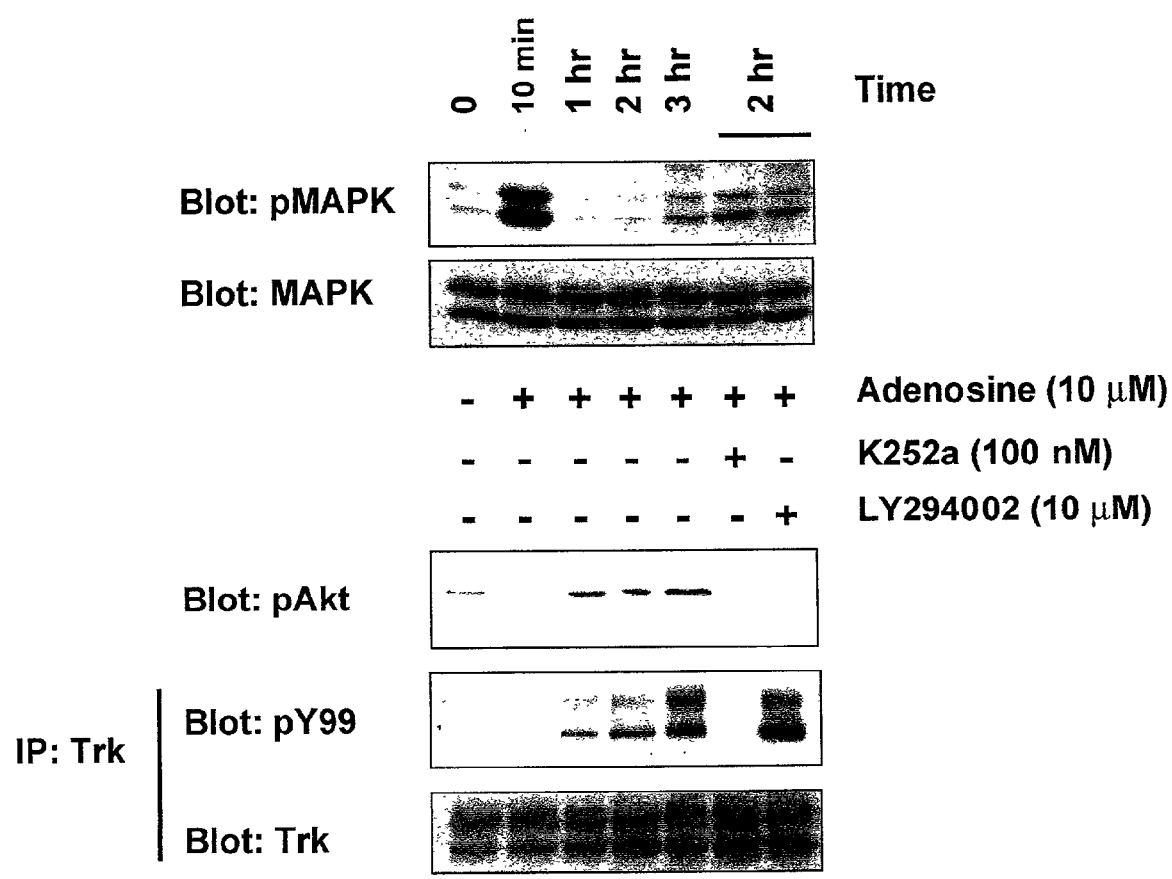
FIG. 5 shows immunoblot analysis on the effects of adenosine upon MAP kinase and Akt activation. PC12 cells (615) were treated with adenosine (10 μM) for various times in the presence or absence of K252a (100 nM) or LY294002 (10 μM). The cells were subsequently harvested in lysis buffer; lysates and immunoprecipitated samples were subsequently immunoblotted with anti-phospho MAP kinase, anti-phospho Akt, and anti-phosphotyrosine. Reprobing with anti-MAP kinase and anti-pan-Trk antibodies was carried out to ensure equal protein loading.

To characterize the signaling pathways activated by adenosine, further experiments were carried out. Pre-treatment with 100 nM K-252a abolished adenosine's activation of TrkA tyrosine kinase activity (FIG. 5). This concentration of K252a has been used to block NGF activation of TrkA receptors (Berg et al, 1992) and the subsequent biological effects of neurotrophins.

Many G protein-coupled receptors activate the MAP kinase pathway. Indeed, within 10 minutes of adenosine treatment, a marked increased in phosphorylated MAP kinase was detected in PC12 cells (FIG. 5), consistent with previous observations (Seidel et al, 1999; Sexl et al, 1997; Gao et al, 1999). After 10 minutes, the levels of activated MAP kinase declined to a baseline level. Activation of MAP kinases can be achieved either by $A_{2A}$-adenosine receptors, or through Trk receptor signaling. To distinguish between these alternatives, PC12 cells were treated with adenosine in the presence and absence of K252a. Using concentrations of K252a that block TrkA signaling, it was found that MAP kinase activity was not altered (FIG. 5). Thus, MAP kinase induction occurs quickly, whereas Trk activation by adenosine followed a slower time course and did not influence MAP kinase activity. This result is in contrast to other examples of G protein-coupled receptor transactivation, in which MAP kinase activities are directly stimulated downstream of the tyrosine kinase receptor (Luttrell et al, 1999).

Another pathway activated by receptor tyrosine kinases is phosphotidylinositol 3'-kinase (PI3-K)/Akt. Interestingly, adenosine (FIG. 5) or CGS 21680 treatment (data not shown) in PC12 cells was also able to activate Akt as detected by a phospho-specific antibody. This response has not been previously associated with adenosine action. The time course of Akt activation was very similar to Trk autophosphorylation induced by adenosine. This effect was eliminated by pretreatment with K252a (100 nM) or LY2494002 (10 µM), a PI3-kinase inhibitor. These results indicate that Akt activation by adenosine is Trk- and PI3-kinase-dependent.

Trophic Effects

Figure 6A:
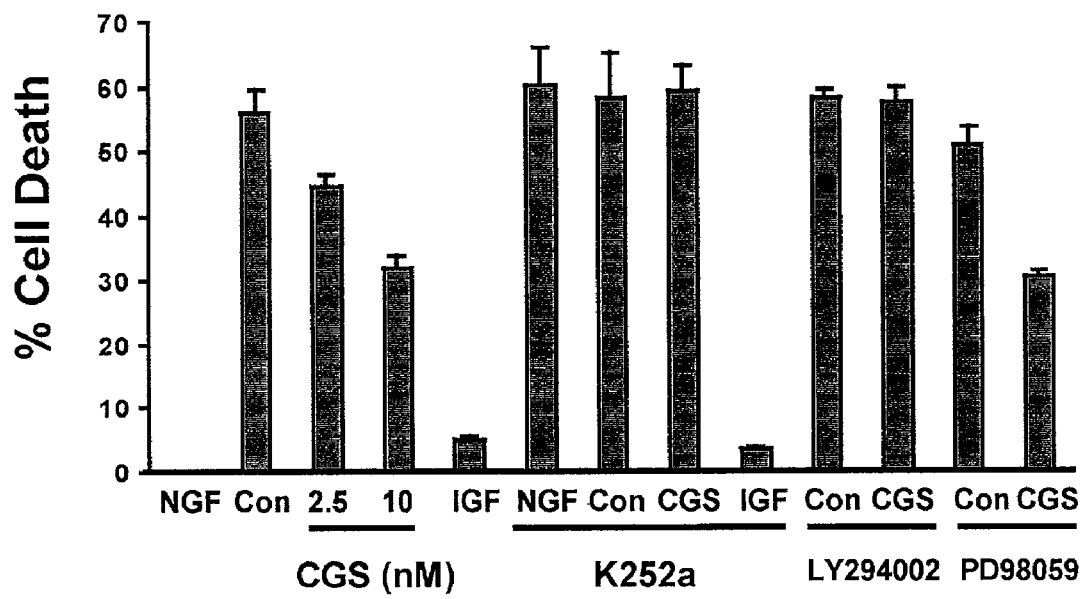
FIGS. 6A and 6B show graphs on the trophic effects of adenosine in PC12 and hippocampal cells deprived of neurotrophins.

To test the functional consequences of adenosine-activated Trk receptor activity, the ability of adenosine to maintain survival of differentiated PC12 cells after withdrawal of NGF was assessed. After culture for 48 hours in the absence of NGF, cell survival was assessed by measuring lactate dehydrogenase (LDH) release. Whereas cells grown without NGF underwent rapid cell death, a one-time treatment with CGS 21680 effectively rescued nearly 50% of the cells (FIG. 6A). The action of CGS 21680 was caused by the activation of Trk receptors, since K252a (100 nM) eliminated the positive effects of CGS 21680 under similar conditions that blocked the activation of Trk receptors (FIG. 5). Likewise, a similar dose of K252a reversed the survival effects of NGF, but not of insulin-like growth factor-1 (IGF-1), in this deprivation assay.

Figure 6B:
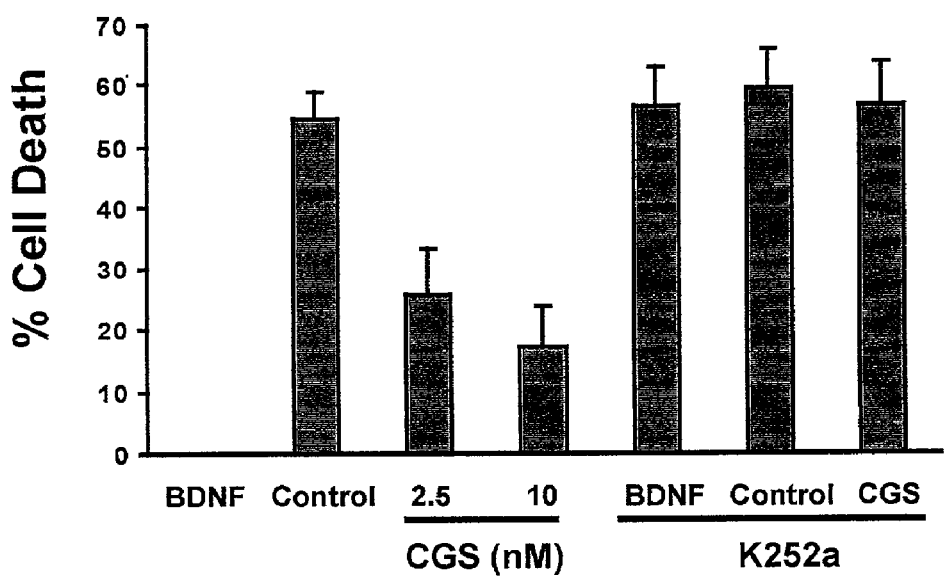

Similar survival results with CGS 21680 were obtained in hippocampal neurons grown in the absence of BDNF (FIG. 6B). The action of CGS 21680 was again dose-dependent and K-252a sensitive. Treatment with CGS 21680 effectively rescued greater than 60% of the cells (FIG. 6B). Hence, a potent adenosine agonist at nanomolar concentrations was able to reverse cell death in both PC12 cells and hippocampal neurons specifically initiated by withdrawal of trophic support by neurotrophins.

The ability of K252a to block adenosine's trophic effect as well as induction of Trk receptor activity suggested that Trk receptor downstream signaling was involved in this process. This was confirmed by the ability of LY294002 to eliminate the trophic effect of CGS 21680 after NGF withdrawal (FIG. 6), indicating that the PI3-kinase/Akt pathway was involved in the survival effects of adenosine. Consistent with the MAP kinase response, the MEK inhibitor PD98059 was not found to have any effect on survival imparted by CGS 21680.

Discussion

Adenosine receptor activation leads to many modulatory effects on neuropeptide and neurotransmitter systems (Sebastiao et al, 2000). These interactions result in effects upon synaptic transmission and neurotransmitter release. A new property of adenosine in neuronal cells that affects neurotrophin signaling is reported here. Through crosstalk with Trk receptor tyrosine kinases, adenosine is capable of activating the PI-3 kinase/Akt cascade, resulting in a survival response in PC12 and hippocampal cells. This response is similar to the effect of NGF and BDNF on their Trk receptors, but differs in the longer time course.

Neurotrophin receptors and $A_{2A}$ receptors have considerable overlap in their central and peripheral nervous system distribution. In the central nervous system (CNS), $A_{2A}$ receptors are expressed in striatum, amygdala, and olfactory tubercles, and in cerebral cortex, hippocampus, and cerebellum (Rosin et al, 1998). All of these regions express TrkB receptors. In the peripheral nervous system (PNS), $A_{2A}$ receptor expression has been localized primarily to dorsal root ganglion and superior cervical ganglion (Kaelin-Lang et al, 1998), two regions that express TrkA receptors. Interestingly, mice deficient in the adenosine $A_{2A}$ receptor display decreased sensitivity to thermal stimulation (Ledent et al, 1997). It is noteworthy that mice with mutations in NGF or TrkA also display hypoalgesia to thermal and mechanical stimuli. These observations suggest that adenosine and neurotrophin signaling may share similar signaling pathways and consequences.

What are the in vivo consequences of these events observed in culture? During hypoxia or ischemic conditions, adenosine is released in large amounts and can act to mediate cellular protection. $A_{2A}$ receptor agonists, such as CGS 21680, have been shown to be neuroprotective against ischemia (Scheardown et al, 1996; von Lubitz et al, 1995) and kainate-induced neuronal damage (Jones et al, 1998) in animals. However, $A_{2A}$ antagonists have been also reported to reduce hypoxic-ischemic neuronal injury (von Lubitz et al, 1995; Phillis 1995). The differential effects of $A_{2A}$ receptor ligands may reflect short term versus long term effects by adenosine receptors (Jacobson et al, 1996). Acute effects of adenosine analogs may lead to opposite effects on neuroprotection than chronic treatment. Engagement of receptor tyrosine kinases such as the Trk subfamily may account for differences in the functional consequences of adenosine action. A distinctive feature of adenosine's transactivation of Trk is the longer time course of Trk mediated signaling, which is similar to neurotrophin-induced signaling.

Adenosine has been proposed as a potential treatment for a wide number of neurological disorders, including cerebral ischemia, sleep disorders, hyperalgesia, Parkinson's disease and other neurodegenerative conditions (Moreau et al, 1999). The findings reported here on adenosine delineate a pathway for activating the neurotrophin signaling system in the absence of neurotrophins. In contrast to other transactivation events involving receptor tyrosine kinases that lead to transient increases in MAP kinase activity, G protein-coupled receptor signaling to neurotrophin receptors leads to selective activation of the PI3-K/Akt pathway over a prolonged time course.

These findings provide a mechanism for the neuroprotective actions of adenosine involving engagement of a G-protein-coupled receptor (the $A_{2A}$ receptor), transactivation of Trk tyrosine kinase receptors, and selective activation of the PI3-K/Akt pathway. A number of approaches have been taken to use neurotrophins to treat Alzheimer's dementia, amyotrophic lateral sclerosis and peripheral sensory neuropathy (Hefti, 1994; Thoenen, 2001). However, there are considerable hurdles in the use of neurotrophic molecules that are related to difficulties in their delivery and pharmacokinetics and unanticipated side effects (Thoenen, 2001). The selective and sustained effects of adenosine on survival signalling pathways suggest that small molecules may be used to target populations of neurons that express both adenosine and Trk receptors. The identification of small ligands in the G protein-coupled receptor family which regulate tyrosine protein kinase activity in neural cells offers a new strategy for promoting trophic effects during normal and neurodegenerative conditions.

This example describes an approach to use small molecule agonists to transactivate Trk neurotrophin receptors. Activation of Trk neurotrophin receptors was observed in PC12 cells and hippocampal neurons after treatment with adenosine, a neuromodulator that acts through G protein-coupled receptors. These effects were reproduced by using the adenosine against CGS 21680 and were counteracted with the antagonist ZM 241385, indicating that this transactivation event by adenosine involves adenosine 2A receptors. The increase in Trk activity could be inhibited by the use of the Src family specific inhibitor, PP1, or K252a, an inhibitor of Trk receptors. In contrast to other G protein-coupled receptor transactivation events, adenosine utilized Trk receptor signaling with a longer time course. Moreover, adenosine activated PI3-K/Akt through a Trk-dependent mechanism that functionally resulted in increased cell survival after NGF or BDNF withdrawal. Therefore, adenosine acting through the $A_{2A}$ receptors exerts a trophic effect through the engagement of Trk receptors.

EXAMPLE 2

Materials and Methods

Immunoprecipitated and Immunoblotting. PC12 (615) cells were maintained in DMEM containing 10% FBS supplemented with 100 units/ml penicillin, 100 μg/ml streptomycin, and 2 mM glutamine plus 200 μg/ml G418. Cells were placed in serum free medium overnight before experiments. Cell lysates from PC12(615) cells, or basal forebrain cells were incubated in lysis buffer (1% Nonidet P-40) for 4 hrs to overnight at 4° C. with anti-pan-Trk polyclonal antibody followed by incubation with protein A-Sepharose beads. Equivalent amounts of protein were analyzed for each condition. The beads were washed five times with lysis buffer, and the immune complexes were boiled in SDS-sample buffer and loaded on SDS-PAGE gels for immunoblot analysis. The immunoreactive protein bands were detected by enhanced chemiluminescence (Amersham Pharmacia).

Basal Forebrain Cell Cultures. Dissociated primary cultures of basal forebrain neurons from embryonic day 18 (E18) rats were prepared from timed-pregnant Sprague-Dawley rats. Fetuses were removed under sterile conditions and kept in PBS on ice for microscopic dissection of the basal forebrain. The meninges were removed and the tissue was placed in Neurobasal media (GIBCO/BRL). The tissue was briefly minced with fine forceps and then triturated with a fire-polished pasteur pipet. Cells were counted and plated on culture wells coated with 0.01 mg/ml poly-D-lysine overnight. Basal forebrain cells were maintained in Neurobasal media, containing B27 supplement and L-glutamine (0.5 mM). Experiments were conducted 10 days after plating.

Results

Figure 7A:
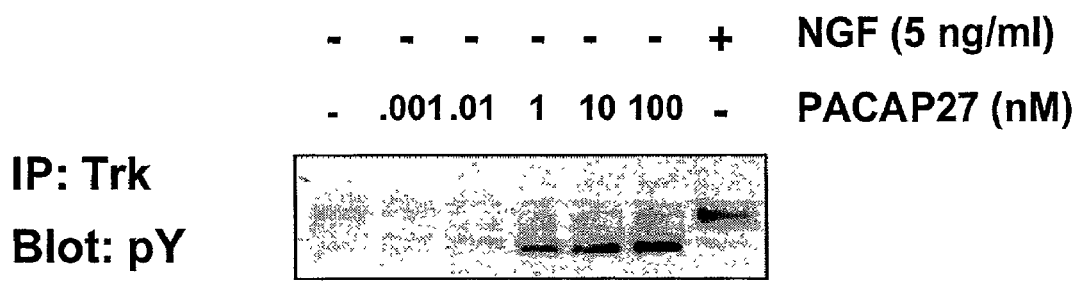
FIGS. 7A and 7B show immunoblot analysis on the time course and dose response of PACAP activation of TrkA receptors.
Figure 7B:
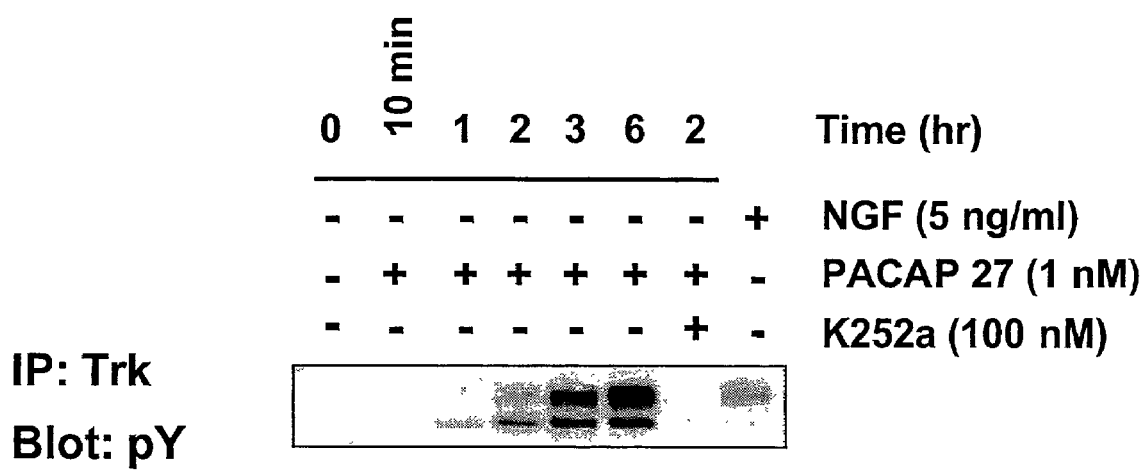

Time Course and Dose Response Curve. The effect of PACAP on TrkA receptor activity occurred in a low nanomolar concentration range (FIG. 7A), consistent with PACAP acting through the PAC1 receptor. A time course of PACAP action showed that the increase in TrkA activation was slow and required 2 hours (FIG. 7B), which is delayed compared with NGF treatment. This increase was blocked by K252a, a well established inhibitor of Trk tyrosine kinases (FIG. 7B).

Figure 8:
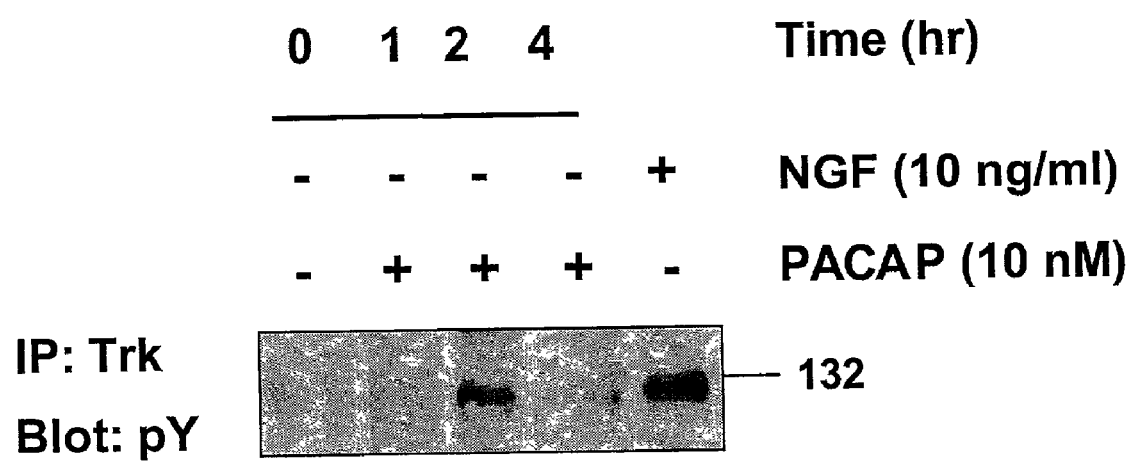
FIG. 8 shows an immunoblot analysis on PACAP activation of TrkA receptors in basal forebrain neurons. Primary cultures of E18 basal forebrain neurons were prepared as described in the Materials and Methods section of Example 2 and treated with PACAP38 (10 nM) or NGF (10 ng/ml) for various times. Activation of TrkA receptors was assessed by immunoprecipitation and Western blotting with anti-phosphotyrosine antibody.

Basal Forebrain. To extend the generality of PACAP's effects on Trk receptors, primary basal forebrain neuronal cultures from E18 rat embryos were established. Basal forebrain neurons predominately express the TrkA receptor and respond to NGF (FIG. 8). These neurons are cholinergic in neurotransmitter properties. Extensive research has previously established that basal forebrain neurons play an important role in cognition and degenerate in Alzheimer's disease (Whitehouse et al., 1982; Coyle et al., 1983; Hefti, 1997; Takei et al., 2000). These neurons also express and PAC1 receptors. Treatment with 10 nM PACAP27 for 2 hours gave rise to phosphorylated TrkA receptors in basal forebrain neurons (FIG. 8). These results demonstrate that effects of PACAP upon primary basal forebrain neurons may be the direct consequence of activation of Trk receptors by PACAP.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aibel et al, "Functional expression of TrkA receptors in hippocampal neurons", *J Neurosci Res* 54(3):424–431 (1998)

Akaike A. et al. "Cholecystokinin-induced protection of cultured cortical neurons against glutamate neurotoxicity", *Brain Res,* 23;557(1–2):303–7 (1991)

Aramori I. et al., "Molecular mechanism of desensitization of the chemokine receptor CCR-5: receptor signaling and internalization are dissociable from its role as an HIV-1 co-receptor" *EMBO J,* 16(15):6055 (1997)

Berg et al, "K-252a inhibits nerve growth factor-induced trk proto-oncogene tyrosine phosphorylation and kinase activity", *J Biol Chem* 267(1):13–16 (1992)

Bonhoeffer T, "Neurotrophins and activity-dependent development of the neocortex", *Curr Opin Neurobiol* 6(1): 119–126 (1996)

Chao and Hempstead et al, "p75 and Trk: a two-receptor system", *Trends Neurosci* ;18(7):321–326 (1995)

Chen Q. et al., "Vasopressin-induced neurotrophism in cultured neurons of the cerebral cortex: dependency on calcium signaling and protein kinase C activity", *Neuroscience*, 101(1) :19–26 (2000)

D'Arcangelo et al, "A branched signaling pathway for nerve growth factor is revealed by Src-, Ras-, and Raf-mediated gene inductions", *Mol Cell Biol* 13(6):3146–3155 (1993)

Daub et al, "Role of transactivation of the EGF receptor in signalling by G-protein-coupled receptors", *Nature* 379 (6565):557–560 (1996)

Dhanasekaran et al., "G protein coupled receptor systems involved in cell growth and oncogenesis", *Endocrinol Rev*, 16:259–270 (1995)

Dixon et al, "Tissue distribution of adenosine receptor mRNAs in the rat", *Br J Pharmacol* 118(6):1461–1468 (1996)

Dobrowsky et al, "Neurotrophins induce sphingomyelin hydrolysis. Modulation by co-expression of p75NTR with Trk receptors", *J Biol Chem* 270(38):22135–22142 (1995)

Edsall et al., "Sphingosine kinase expression regulates apoptosis and caspase activation in PC12 cells", *J Neurochem*, 76(5):1573–84 (2001)

Etschied et al., *Br. J. Pharmacol.*, 103:1347–1350 (1991)

Firestein S. "How the olfactory system makes sense of scents", *Nature*, 13:413, 211–218 (2001)

Forloni G. et al., "Protective effect of somatostatin on nonapoptotic NMDA-induced neuronal death: role of cyclic GMP", *J Neurochem*, 68(1):319–27 (1997)

Gallo et al, "The trkA receptor mediates growth cone turning toward a localized source of nerve growth factor", *J Neurosci* 17(14):5445–5454 (1997)

Gao et al, "A2B adenosine and P2Y2 receptors stimulate mitogen-activated protein kinase in human embryonic kidney-293 cells. cross-talk between cyclic AMP and protein kinase c pathways", *J Biol Chem* 274(9):5972–5980 (1999)

Gu et al, "Apoptotic signaling through the beta-adrenergic receptor. A new Gs effector pathway", *J Biol Chem* 275(27):20726–20733 (2000)

Guderman et al., "Functional and structural complexity of signal transduction via G-protein-coupled receptors. *Ann. Rev. Neurosci.*, 20:399–427 (1997)

Guderman T., "Multiple pathways of ERK activation by G protein-coupled receptors", *Novartis Foundation Symp*, 239:68–79 (2001)

Gurwitz D. et al., "NGF-dependent neurotrophic-like effects of AF102B, an M1 muscarinic agonist, in PC12M1 cells", *Neuroreport*, 15;6(3):485–8 (1995)

Hasenohrl R. et al., "Substance P and its role in neural mechanisms governing learning, anxiety and functional recovery", *Neuropeptides*, 34(5):272–80 (2000)

Hanke et al, "Discovery of a novel, potent, and Src family-selective tyrosine kinase inhibitor. Study of Lck- and FynT-dependent T cell activation", *J Biol Chem* 271(2) :695–701 (1996)

Hefti F, "Neurotrophic factor therapy for nervous system degenerative diseases", *J Neurobiol* 25(11):1418–1435 (1994)

Hempstead et al, "Expression of functional nerve growth factor receptors after gene transfer", *Science* 243(4889): 373–375 (1989)

Hempstead et al, "Overexpression of the trk tyrosine kinase rapidly accelerates nerve growth factor-induced differentiation", *Neuron* 9(5):883–896 (1992)

Inoue et al., *Eur. J. Pharmacol.*, 215:321–324 (1992)

Ishige K. et al., "The activation of dopamine D4 receptors inhibits oxidative stress-induced nerve cell death", *J Neurosci*, 15;21(16):6069–76 (2001)

Iwasaki Y et al., "Trophic effect of angiotensin II, vasopressin and other peptides on the cultured ventral spinal cord of rat embryo" *J Neurol Sci*, 103(2):151–5 (1991)

Jacobson et al, "Adenosine receptor ligands: differences with acute versus chronic treatment", *Trends Pharmacol Sci* 17(3):108–113 (1996)

Jarvis et al, "[3H] CGS 21680, a selective A2 adenosine receptor agonist directly labels A2 receptors in rat brain", *J Pharmacol Exp Ther* 251(3):888–893 (1989)

Jones et al, "Protection against kainate-induced excitotoxicity by adenosine A2A receptor agonists and antagonists", *Neuroscience* 85(1):229–237 (1998)

Kaelin-Lang et al, "Expression of adenosine A2a receptor gene in rat dorsal root and autonomic ganglia", *Neurosci Lett* 246(1):21–24 (1998)

Kaplan D R, Miller F D. "Neurotrophin signal transduction in the nervous system" *Curr Opin Neurobiol.*, 10(3): 381–91 (2000)

Kim, A., Sheline, C., Tian, M., Higashi, T., McMahon, R., Cousins, R. & Choi, D. *Brain Res* on-line published (2000)

Kim et al., "Akt phosphorylates and negatively regulates apoptosis signal-regulating kinase 1", *Mol Cell Biol*, 21:893–901 (2001)

Kim et al., *J. Biol. Chem.*, 269:6471–6477 (1994)

Le et al., "Are dopamine receptor agonists neuroprotective in Parkinson's disease?" *Drugs Aging*, 18(6):389–96 (2000)

Ledent et al, "Aggressiveness, hypoalgesia and high blood pressure in mice lacking the adenosine A2a receptor", *Nature* 388(6643):674–678 (1997)

Levi-Montalcini R, "The nerve growth factor 35 years later", *Science* 237(4819):1154–1162 (1987)

Lewin et al, "Physiology of the neurotrophins", *Annu Rev Neurosci* 19:289–317 (1996)

Linseman et al., *J. Biol. Chem.*, 270:12563–12568 (1995)

Luttrell et al, "Regulation of tyrosine kinase cascades by G-protein-coupled receptors", *Curr Opin Cell Biol* 11(2): 177–183 (1999)

Lyons et al, Brain-derived neurotrophic factor-deficient mice develop aggressiveness and hyperphagia in conjunction with brain serotonergic abnormalities", *Proc Natl Acad Sci USA* 96(26):15239–15244 (1999)

Martucciello et al., "Pathogenesis of Hirschsprungs's disease", *J Pediatr Surg*, 35(7):1017–1025 (2000)

McAllister et al, "Neurotrophins and synaptic plasticity", *Annu Rev Neurosci* 22:295–318 (1999)

Messer et al., "Role for GDNF in biochemical and behavioral adaptations to drugs of abuse", *Neuron*, 26(1): 247–257 (2000)

Minichiello et al, "Essential role for TrkB receptors in hippocampus-mediated learning", *Neuron* 24(2):401–414 (1999)

Montmayeur J P. et al., "A candidate taste receptor gene near a sweet taste locus", *Nature Neurosci*, 4(5):492–498 (2001)

Moreau et al Central adenosine A(2A) receptors: an overview", *Brain Res Brain Res Rev* 31(1):65–82 (1999)

Neary et al, "Trophic actions of extracellular nucleotides and nucleosides on glial and neuronal cells", *Trends Neurosci* 19(1): 13–18 (1996)

Offen D. et al., "Vasoactive intestinal peptide (VIP) prevents neurotoxicity in neuronal cultures: relevance to neuroprotection in Parkinson's disease", *Brain Res,* 31:854(1–2): 257–62 (2000)

Phillis J, "The effects of selective A1 and A2a adenosine receptor antagonists on cerebral ischemic injury in the gerbil", *Brain Res* 705(1–2):79–84 (1995)

Poucher et al, "125I-4-(2-[7-amino-2-[2-furyl][1,2,4]triazolo[2,3-a][1,3,5]triazin-5-yl-amino]ethyl)phenol, a high affinity antagonist radioligand selective for the A2a adenosine receptor", *Mol Pharmacol* 48(6):970–974 (1995)

Ralevic et al, "V Receptors for purines and pyrimidines", *Pharmacol Rev* 50(3):413–492 (1998)

Rao et al., *J. Biol. Chem.*, 270::27871–27875 (1995)

Reppert, S M. et al., "Melatonin receptors step into the light: cloning and classification of subtypes", *Trends in Pharmacol Sci,* 17:100–102 (1996)

Rosin et al, "Immunohistochemical localization of adenosine A2A receptors in the rat central nervous system", *J Comp Neurol* 401(2):163–186 (1998)

Scheardown, M. & Knutsen, L. (1996) *Drug Dev Res* 39, 108–114

Sebastiao et al, "Fine-tuning neuromodulation by adenosine", *Trends Pharmacol Sci* 21(9):341–346 (2000)

Seidel et al, "Activation of mitogen-activated protein kinase by the A(2A)—adenosine receptor via a rap1-dependent and via a p21(ras)—dependent pathway", *J Biol Chem* 274(36):25833–25841 (1999)

Sexl et al, "Stimulation of the mitogen-activated protein kinase via the A2A-adenosine receptor in primary human endothelial cells" *J Biol Chem* ;272(9):5792–5799 (1997)

Strahs D. et al., "Comparative modeling and molecular dynamics studies of the delta, kappa and mu opioid receptors", *Protein Eng,* 10(9): 1019–1038 (1997)

Striggow F. et al., "Four types of protease-activated receptors are widely expressed in the brain and are up-regulated in hippocampus by severe ischemia", *Europ J Neurosci,* 14:595–608 (2001)

Thoenen H, "Neurotrophins and neuronal plasticity", *Science* 270(5236) :593–598 (1995)

Thoenen, H. In: *Axonal Regeneration in the Central Nervous System*, eds. Ingoglia, N. and Murray, M., Dekker, New York, pp. 675–697, (2001)

van Biesen et al., "Mitogenic signaling via G protein-coupled receptors, *Endocrinol Rev,* 17:690–714 (1996)

von Lubitz et al, "Cerebral ischemia in gerbils: effects of acute and chronic treatment with adenosine A2A receptor agonist and antagonist", *Eur J Pharmacol* 287(3):295–302 (1995)

Williams et al, "Characterization of adenosine receptors in the PC12 pheochromocytoma cell line using radioligand binding: evidence for A-2 selectivity", *J Neurochem* 48(2):498–502 (1987)

Yan W. et al., "5-HT1a receptors mediate the neurotrophic effect of serotonin on developing dentate granule cells", *Brain Res Dev Brain Res,* 20;98(2):185–90 (1997)

Yasuyoshi H. et al., "Protective effect of bradykinin against glutamate neurotoxicity in cultured rat retinal neurons" *Invest Ophthalmol Vis Sci,* 41(8):2273–8 (2000)

Yoon et al, Competitive signaling between TrkA and p75 nerve growth factor receptors determines cell survival", *J Neurosci* 1;18(9):3273–3281 (1998)

What is claimed is:

1. A method for screening and identifying molecules that mediate neuronal cell survival in the absence of neurotrophic factors and transactivate a neurotrophic receptor, comprising assay A or assay A in combination with either or both of assay B and assay C, wherein:

assay A comprises:

treating neuronal cells, PC12 cells, or N2a neuroblastoma cells with a candidate transactivator molecule;

reacting the neurotrophic receptor, obtained from a cell lysate of the treated cells, with an anti-phosphotyrosine antibody specific for the phosphorylated form of the neurotrophic receptor; and detecting binding of the anti-phosphotyrosine antibody to the phosphorylated form of the neurotrophic receptor to identify a transactivator molecule of the neurotrophic receptor that mediates neuronal cell survival in the absence of neurotrophins by transactivating the neurotrophic receptor;

assay B comprises:

treating neuronal cells, PC12 cells, or N2a neuroblastoma cells with a candidate transactivator molecule;

reacting either phosphotidylinositol 3'-kinase (PI3-K), obtained from a cell lysate of the treated cells, with an anti-phospho-PI3-K antibody specific for the phosphorylated form of PI3-K or Akt, obtained from a cell lysate of the treated cells, with an anti-phospho-Akt antibody specific for the phosphorylated form of Akt; and detecting binding of the anti-phospho-PI3-K antibody to the phosphorylated form of PI3-K or binding of the anti-phospho-Akt antibody to the phosphorylated form of Akt to identify a transactivator molecule of the neurotrophic receptor and its downstream Akt target; and assay C comprises:

culturing neuronal cells, PC12 cells, or N2a neuroblastoma cells in the presence of neurotrophic factors;

treating and culturing the cells with a candidate transactivator molecule in the absence of neurotrophic factors; and determining the level of cell survival to identify a transactivator molecule of the neurotrophic receptor, wherein an increase in cell survival, or a decrease in cell death, over a control in which the cells are cultured in the absence of neurotrophic factors and the candidate transactivator molecule, identifies a transactivator molecule.

2. The method of claim 1, wherein the neurotrophic receptor is a Trk receptor.

3. The method of claim 2, wherein the Trk receptor is TrkA receptor.

4. The method of claim 3, wherein the cells are PC12 cells.

5. The method of claim 1, wherein the candidate transactivator molecule is a ligand of a G protein coupled receptor (GPCR).

6. The method of claim 1, wherein the neurotrophic receptor is a Ret receptor.

7. The method of claim 6, wherein the cells are N2a neuroblastoma cells.

8. The method of claim 1, wherein, in the reacting and detecting steps of assay B, Akt is reacted with anti-phospho-Akt antibody and binding of anti-phospho-Akt antibody to the phosphorylated form of Akt is detected.

9. The method of claim 8, wherein assay B further comprises:

reacting Akt, obtained from a cell lysate of the treated cells, with an anti-Akt antibody; and detecting binding of the anti-Akt antibody to Akt.

10. The method of claim 1, wherein in the reacting and detecting steps of assay B, PI3-K is reacted with anti-phospho-PI3-K antibody and binding of anti-phospho-PI3-K antibody to the phosphorylated form of PI3-K is detected.

11. The method of claim 10, wherein assay B further comprises:

reacting PI3-K, obtained from a cell lysate of the treated cells, with an anti-PI3-K antibody; and detecting binding of the anti-PI3-K antibody to PI3-K.

* * * * *